US006423672B1

(12) United States Patent
Shafer et al.

(10) Patent No.: US 6,423,672 B1
(45) Date of Patent: Jul. 23, 2002

(54) PROCESS FOR MAKING SOAP BAR COMPRISING ABOUT 6% AND GREATER TRIGLYCERIDES

(75) Inventors: Georgia Shafer, Garfield, NJ (US); Michael Massaro, Congers, NY (US); Yury Yarovoy, Berkeley Heights; William Lanza, Towaco, both of NJ (US)

(73) Assignee: Unilever Home & Personeal Care USA division of Conopco, Inc., Greenwich, CT (US)

( * ) Notice: Subject to any disclaimer, the term of this patent is extended or adjusted under 35 U.S.C. 154(b) by 6 days.

(21) Appl. No.: 09/845,109

(22) Filed: Apr. 26, 2001

(51) Int. Cl.[7] .................................................. A61K 7/50

(52) U.S. Cl. ....................... 510/151; 510/152; 510/153; 510/155; 510/156; 510/458; 510/459; 510/460

(58) Field of Search ................................ 510/141, 151, 510/152, 153, 155, 156, 458, 459, 460

(56) References Cited

U.S. PATENT DOCUMENTS

| | | | | |
|---|---|---|---|---|
| 3,814,698 | A | 6/1974 | Ferrara | |
| 3,941,712 | A | 3/1976 | Ferrara et al. | |
| 4,582,626 | A | 4/1986 | Ferrara | |
| 5,952,276 | A | 9/1999 | DeFerran et al. | |
| 6,242,398 | B1 * | 6/2001 | Chambers et al. | 510/151 |
| 6,255,265 | B1 * | 7/2001 | Van Gunst et al. | 510/152 |

* cited by examiner

*Primary Examiner*—Necholus Ogden

(57) ABSTRACT

The invention relates to soap bars comprising 6% to 13% triglyceride oils wherein said bars simultaneously have post processing properties and maintain good lather. In a second embodiment, the invention relates to a process of making predominantly soap bars having noted properties comprising adding 6 to about 13% by wt. triglyceride oil(s) at finishing stage post crystallization.

2 Claims, No Drawings

PROCESS FOR MAKING SOAP BAR COMPRISING ABOUT 6% AND GREATER TRIGLYCERIDES

FIELD OF THE INVENTION

The present invention relates to a process for making predominantly soap based bars having about 6% by wt. or more (up to about 13% by wt.) of specific oils (i.e., triglyceride oils) which both process well (e.g., as measured by bar integrity, yield/++-stress) and retain desirable users properties (e.g., lather) as per specifically defined tests.

BACKGROUND OF THE INVENTION

Traditionally, emollient oils (e.g., mineral oils, silicones, emollients esters) have been incorporated into soap bars at relatively low levels, or, less that 5.0% by wt. Higher levels are generally avoided to avoid problems in processability and/or in user properties (e.g., mineral oils lather poorly). At such levels, however, there is little discernible sensory effect. Typical of such bars having emollient levels of up to 5% is U.S. Pat. No. 5,952,276 to de Ferran et al.

One reason why higher oils levels have not been used is because it has been traditionally difficult to add such high levels during soap milling step (i.e., the point in processing when other additives, such as colorants or odorants, have been added) or any time after cooling and when, accordingly, solidification has begun.

Theorizing that the difficulty of adding high levels of additives to bar at the milling step may be correlated to difficulties arising once crystal structure has formed, U.S. Pat. No. 3,814,698 to Ferrara et al. and U.S. Pat. No. 3,941,712 to Ferrara et al., disclose compositions having much higher levels of "bath oil" wherein the bath oil is added at bar saponification step (when ingredients are liquid) rather than milling step.

In both Ferrara patents, the bath oil is broadly defined to include materials such as oils, esters, waxes, long chain alcohols etc. No one material or class is identified as better than another and the only caveat is that, in order to incorporate the amounts of bath oil contemplated by the subject invention, the oil should be added at saponification step. As noted, this is believed to have something to do with the fact that there is no crystal structure at that point (U.S. Pat. No. 3,814,698 at column 2, lines 66–68).

U.S. Pat. No. 4,582,626 to Ferrara discloses that a slip agent should be added at the same time as the bath oil (column 3, lines 6–12). The slip agent and emollient, however, are again added to the saponification mixture (column 3, lines 14–17). Further, again no one material is said to be better than another.

Unexpectedly applicants have found that, if specific emollient oils are chosen (e.g., sunflower oil, castor, palm kernel oil, corn, olive, safflower, cottonseed and/or mixtures thereof), relatively large amounts (e.g., 6% by wt. to 13% of oil) may be incorporated.

While not wishing to be bound by theory, it is believed the selected oils are readily absorbed into the mortar liquid crystal phase such that they do not form separate phase (which could interact with soap and disrupt processing properties such as bar integrity or yield stress) and, at the same time, are readily delivered from the bar to provide good user properties.

Thus, in one embodiment, this invention relates to a predominantly soap bar comprising about 59 to 84% soap, 0 to 10% non-soap, non-triglyceride agents (e.g., filler, processing aids, cost reducing agents, skin conditioning agents, none of which categories are necessarily exclusive of the others), 10 to 18% water and 6 to 13% triglyceride oil, wherein said triglyceride oil is added directly at finishing stage, post crystallization such that combination of components yields bar with minimal yield stress of about 90, preferably about 100 and lather volume of at least about 65%, preferably at least 70% relative to bars of the soap base.

In a second embodiment (that of subject specification), the invention relates to a process for making a bar comprising predominantly soap (59% to 84% soap), 0 to 10% non-soap, non-triglyceride agents and 10 to 18% water wherein said bar has minimal yield stress of about 90, preferably about 100 and lather volume of at least about 65%, preferably at least 70% of the soap base, wherein said process comprises adding about 6% to 13% triglyceride oil to the bar at a finishing stage when other components have already crystallized

BRIEF DESCRIPTION OF THE INVENTION

In one embodiment, the invention provides a bar composition comprising:

(a) 59 to 84% by wt. soap;

(b) 0 to 10% by wt. of non-soap non-triglyceride agents (for example, used to enhance processing, reduce costs and/or improve skin conditioning) (examples of such agents include fillers, glycerin, PEG, polymers, free fatty acids, synthetic surfactants);

(c) 10 to 18% by wt. water; and (d) 6 to 13% triglyceride oil, wherein oil is added directly at finishing stage post crystallization such that said bar has minimal yield stress of about 90, preferably 100 and lather volume of at least about 65% relative to base bar.

In a second embodiment, the invention provides a process for making a bar comprising:

(a) 59 to 84% by wt. soap;

(b) 0 to 10% non-soap, non-triglyceride agents; and (c) 10 to 18% water, wherein said bar has minimal yield stress of about 90, preferably 100 and lather volume of at least 65% relative to base bar, wherein said process comprises adding 6% to 13% triglyceride oil to the bar at a finishing stage when other bar components have already crystallized.

DETAILED DESCRIPTION OF THE INVENTION

The present invention relates to process for making compositions comprising relatively large amounts of triglyceride oils. The oils can be incorporated at a point beyond the saponification stage (i.e., they can be incorporated at finishing stage, post crystallization) without hindering processing (as measured, for example by yield stress and bar integrity) and while retaining desirable consumer attributes (e.g., lathering).

In one embodiment, the invention relates to compositions, e.g., soap based compositions, comprising specific emollient oils. Unexpectedly, it has been found that when certain oils (i.e., triglyceride emollients) are incorporated into bars at the so-called "finishing" steps of bar preparation (i.e., once bars have reached stage where soap noodles are fully crystallized), certain benefits are found. Specifically, when incorporated at this finishing stage, the triglyceride oils process well while providing good lather as defined.

The bar composition of the invention comprises 59% to 84%, preferably 70 to 80% by wt. soap.

The term "soap" is used herein in its popular sense, i.e., the alkali metal or alkanol ammonium salts of aliphatic, alkane-, or alkene monocarboxylic acids. Sodium, potassium, magnesium, mono-, di- and tri-ethanol ammonium cations, or combinations thereof, are suitable for purposes of this invention. In general, sodium soaps are used in the compositions of this invention, but from about 1% to about 25% of the soap may be potassium or magnesium soaps. The soaps useful herein are the well known alkali metal salts of natural of synthetic aliphatic (alkanoic or alkenoic) acids having about 8 to 22 carbon atoms, preferably about 8 to about 18 carbon atoms. They may be described as alkali metal carboxylates of acrylic hydrocarbons having about 8 to about 22 carbon atoms.

Soaps having the fatty acid distribution of coconut oil may provide the lower end of the broad molecular weight range. Those soaps having the fatty acid distribution of peanut or rapeseed oil, or their hydrogenated derivatives, may provide the upper end of the broad molecular weight ranges.

It is preferred to use soaps having the fatty acid distribution of coconut oil or tallow, or mixtures thereof, since these are among the more readily available fats. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principle chain lengths are C16 and higher. Preferred soap for use in the compositions of this invention has at least about 85% fatty acids having about 12 to 18 carbon atoms.

Coconut oil employed for the soap may be substituted in whole or in part by other "high-alluric" oils, that is, oils or fats wherein at least 50% of the total fatty acids are composed of lauric or myristic acids and mixtures thereof. These oils are generally exemplified by the tropical nut oils of the coconut oil class. For instance, they include: palm kernel oil, babassu oil, ouricuri oil, tucum oil, cohune nut oil, murumuru oil, jaboty kernel oil, khakan kernel oil, dika nut oil and ucuhuba butter.

A preferred soap is a mixture of about 30% to about 40% coconut oil and about 60% to about 70% tallow. Mixtures may also contain higher amounts of tallow, for example, 15% to 20% coconut and 80% to 85% tallow.

The soaps may contain unsaturation in accordance with commercially acceptable standards. Excessive unsaturation is normally avoided.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric ($C_{12}$), myristic ($C_{14}$), palmitic ($C_{16}$), or stearic ($C_{18}$) acids with an alkali metal hydroxide or carbonate.

The bar compositions may optionally comprise 0% to 10% by wt. of optional components which are neither glyceride, soap or water. If synthetic surfactant is used, it may be selected form the group consisting of anionic, nonionic, amphoteric/zwitterionic and cationic surfactants.

Anionic may be an aliphatic sulfonate (e.g., $C_8$ to $C_{22}$ alkane sulfonate or disulfonate; or aromatic sulfonate), alkyl sulfate, alkyl ether sulfate, alkyl sulfosuccinate, alkyl or acyl taurate, alkyl or acyl sarcosinates or any of the anionics described, for example, in U.S. Pat. No. 5,916,856 to Massaro et al., hereby incorporated by reference into the subject application.

Similarly amphoterics, nonionics and cationics may be any of the surfactants described in U.S. Pat. No. 5,916,856 to Massaro et al.

Other agents which may be used include processing aid (e.g., filler) or conditioning agents (e.g., PEG, free fatty acid or glycerin).

Other additives which may be used include one more of the following preservatives: perfumes, colors, opacifiers, optical brighteners, germicides.

The bar also comprises 10 to 18% by wt., preferably 10 to 15% by wt. water.

Finally, the compositions comprise 6% to 13% by wt. of triglyceride oil.

Examples of triglycerides which may be used include apricot oil, sunflower seed oil, avocado oil, castor oil, cottonseed oil, palm kernel oil, safflower oil, corn oil, soya bean oil, almond oil, wheat germ and/or blends thereof.

The oils of the invention are added in the finishing stages of soap making.

More specifically, milled soaps have been made for many years. It is usual to produce such soaps by liquefying a mixture of fatty acid, or acids, or glycerides thereof, and aqueous sodium hydroxide solution at elevated temperatures; saponifying the fatty acid content of the warm liquid mixture; cooling the saponification mixture to a substantially solid, but suitable soft, condition, forming the solidified saponification mixture into a suitable shape, e.g., by extrusion into a ribbon or the like; drying the shaped extrudate to an acceptable moisture content; milling the dried "soap" with conventional additives and adjuvants such as dyes, pigments, perfumes and the like; and then forming the milled soap composition into bars or other desired shapes.

The oils of the invention as noted, are added, at finishing stage, post crystallization.

In a second embodiment of the invention (that of subject specification), the invention comprises a process for making bars comprising soap; non-soap, non-triglyceride components and water in amounts noted above and wherein bar has minimal yield stress and minimal lather volumes as also noted, wherein said process comprises adding 6% to 13% triglyceride oil to the bar at a finishing stage post crystallization of the non-triglyceride components.

It should be noted that other minors (e.g., perfume) may also be added after crystallization as long as at least sufficient components have been added (e.g., soap and structurant) to form a crystallized soap base.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight.

EXAMPLES

Protocol

Yield Stress Measurement

A weighted "cheese-wire" is allowed to cut at a right angle across an edge of a soap sample, often a billet. As the wire moves into the soap so the length of wire in the soap will increase until it reaches an equilibrium position. At this point the downward force from the weight on the wire is balanced by the upward force from the viscous drag of the soap on the wire. The yield stress of the soap can be calculated from the length of the cut, the wire diameter and the applied weight. It is important that the soap temperature is also measured. For comparisons, yield stress at the measured temperature is normally converted mathematically to yield stress at a specified temperature of 40° C.

To run yield stress test, a section of stainless steel wire is attached to a counter-balanced arm which can pivot freely via a ball-race bearing. Soap billets are supported on a metal or wooden block with a V-shaped indentation.

The wire should be stainless and that the wire diameter should be measured only after the wire has been tensioned.

By applying a weight (W g) directly above the cheese wire, a constant force is exerted on the wire which will slice into the soap. The area over which the force acts increases as the depth of cut increases, and therefore the stress being exerted decreases until it is exactly balanced by the resistance of the soap and the wire stops moving. The stress at this point is equal to the yield stress of the soap. The time taken to reach this point has been found to be ~30 secs so that a standard time of 1 min is generally chosen to ensure that the yield stress has been reached. After this time the weight is removed and the length of the cut measured.

The yield stress is calculated using the semi-empirical formula:

$$\text{Yield stress} = 3/8\frac{W\times 98.1}{1\times d}Nm^{-2} \text{ or}$$

-continued $$\text{Yield stress} = 0.000368\times\frac{W}{l\times d}Nm^{-2}\times 10^{5}$$

where l and d are the length of cut and diameter of the wire respectively (both measured in cm).

If the actual sample temperature is greater than 40° C. then the following equation can be used to correct the yield stress to a value of 40° C.

$$YS_{40} = YS_T\times e^{b}$$

$$\text{Where } e = 2.718$$

$$b = 16.87\times\frac{T-40}{273-T}$$

Any measurement of yield stress will be highly influenced by product temperature. A good practice is to determine yield stress/temperature at the time of plodding, and again using a bar equilibrated to 40° C. in an occlusive wrapping of polythene and aluminum cooking foil.

Lather Volume Test

The amount of lather generated by a toilet soap is an important parameter affecting consumer preference. The lather volume test described here gives a measure of lather generation under standard conditions, thus allowing objective comparison of different soap formulations.

Lather is generated by trained technicians using a standardized method. The lather is collected and its volume measured. A subjective assessment of lather creaminess is made by the technicians during the generation of the lather.

Typical equipment used is as follows.

| | |
|---|---|
| Washing up bowl | 1 per operator<br>capacity 10–15 liters |
| Soap drainer dishes | 1 per sample |
| Surgeons' rubber gloves | British Standard BS 4005 or equivalent<br>range of sizes to fit all technicians |
| Tall cylindrical glass beaker or wide measuring cylinder | 500–1000 ml capacity graduated in 10 ml intervals |
| Thermometer | Mercury types are not approved |
| Glass rod | Sufficiently long to allow stirring in the calibrated glass beaker |

The procedure is typically as follows:

i. Tablet pretreatment: Wearing the specified type of globe worn inside out and well washed in plain soap, wash down all test tablets at least 10 minutes before starting the test sequence. This is best done by twisting them about 20 times through 180° C. under running water;

ii. Place about 5 liters of water of known hardness and at a specified temperature (typically 20–40° C.) in a bowl. Change the water after each bar of soap has been tested;

iii. Take up the tablet, dip it in the water and remove it. Twist the tablet 15 times, between the hands, through 180° C. Replace the tablet on the soap dish;

iv. The lather is generated from the soap remaining on the gloves:

Stage 1: Rub the tips of the fingers of one hand (either hand) on the palm of the other hand 10 times;

State 2: Grip the right hand with the left, or vice versa, and force the lather to the tips of the fingers. Repeat with the hands reversed. This operation is repeated five times with each hand.

Repeat Stages 1 and 2;
Place the lather in the calibrated beaker.

v. Repeat the whole procedure of lather generation from paragraph iii. Twice more, combining all the lather in the beaker;

vi. Stir the combined lather gently to release large pockets of air. Read and record the volume.

The lather volume results may be assessed using a paired comparison and a value of least significant difference (LSD). Typically, six results for each bar are averaged, and paired comparisons carried out between the averaged results for each bar. If the lather volume differs by more than the LSD then the products are said to produce "significantly different amounts of lather". This LSD value is obtained from 50 separate lather assessments of standard control samples (i.e., 5 different batches: 10 samples per batch) carried out at the same temperature.

Calculations are then made as follows:

i.

$$\text{Calculate variance } \sigma^2 = \frac{1}{n-1}\left[\sum X_i^2 - \frac{1}{n}\left(\sum X_i\right)^2\right]$$

ii. Look up t tables (n=50, p=0.05)

iii. Calculate the least significant difference from the equation $$\text{L.S.D.} = t\frac{2\cdot\sigma^2}{n}$$

Example 1–4 and Comparative A–E

In order to show the advantages in bar processing (e.g., yield stress, integrity) and lather relative to use of other oils, applicants prepared the following Tables 1 and 2.

TABLE 2

| | Emollient | User Property Lather, % | Bar Property Yield Stress | Processing Integrity | Overall +/− |
|---|---|---|---|---|---|
| A | Base 85/15 | +(100) | +(203) | + | + |
| B | Fatty Acid | +(150) | −(31) | − | − |
| C | Alkyl Ester (IPM) | −(60) | −(72) | + | − |
| 1 | SFO | +(100) | +(122) | + | + |
| 2 | PKO | +(80) | +(95) | + | + |
| 3 | Corn Oil | +(70) | +(122) | + | + |
| 4 | Soybean Oil | +(70) | +(136) | + | + |
| D | Mineral Oil | −(40) | +(122) | + | − |
| E | Silicone Oil | −(60) | +(122) | + | − |

Table 1 sets forth examples of base alone (Comparative A) and examples of 4 classes of non-glyceride oils (Comparatives B–E) as well as examples of 4 types of triglyrides (Examples 1–4). Each of the non-triglycerides and triglycerides were used in an amount of 10% by wt. total composition (except Comparative A wherein no oil is used).

For purposes of the example, the bars comprised fatty acid and water (about 12–13% by wt.) or fatty acid, oil and water. It should be understood, however, that small amounts of non-soap and non-oil agents, as described in the specification, may be used.

The values for yield stress and lather (as obtained using cheesewire measurements) and comments about whether bar had integrity are noted in Table 1 and the various results are compiled in Table 2.

As clearly seen from Table 2, it is only triglyceride oil which simultaneously maintain yield stress of at least about 90, lather at greater than about 65% relative to base and maintain bar integrity. As noted from Table 1 integrity data, SFO and PKO (Examples 1 and 2) are particularly preferred.

Examples 10–12 and Comparative F

In order to show the effect of varying levels of triglycerides, applicants conducted test using base bar and varying amounts (7.5 to 15% by wt.) of sunflower oil.

TABLE 1

Bars with Hydrophobic Emollients

| | Comparative A - Base 85/15* | Comparative B - Fatty Acid (Coco Fatty Acid) | Comparative C - Alkyl Ester Isopropyl Myristrate | Example 1 (Sunflower Seed Oil) | Example 2 (Palm Kernel Oil) | Example 3 (Corn Oil | Example 4 (Soybean Oil) | Comparative D (Hydrocarbon Mineral Oil) | Comparative E (Silicone PDMS) |
|---|---|---|---|---|---|---|---|---|---|
| Throughput | 145 | | 175 | 192 | 115 | 134 | 141 | 192 | 185 |
| Wire Penetration | 0.6 | 4.0 | 1.7 | 1 | 1.3 | 1.0 | 0.9 | 1 | 1 |
| Yield Stress | 203 | 31 | 72 | 122 | 95 | 122 | 136 | 122 | 122 |
| Integrity | Yes | No | No | Yes | Yes | Yes (some cracks) | Yes (some cracks) | Yes | Yes |
| Lather | 50 | 75 | 30 | 50 | 40 | 35 | 34 | 20 | 30 |
| Lather % vs. Base | 100 | 150 | 60 | 100 | 80 | 70 | 70 | 40 | 60 |

*Referring to soap base having about 85% tallow blend (predominantly $C_{16}$–$C_{18}$) and about 15% coconut blend (predominantly $C_{12}$ fatty acid soap). This bar is not superfatted as in Comparative B.

Results are set forth in Table 3 below.

TABLE 3

Effect of the Triglyceride Level on Bar Properties
85/15 Soap Base + SFO

| Example | Wt. % of SFO | Lather | Yield Stress | Comments |
|---|---|---|---|---|
| 10 | 7.5 | 90 | 135 | Hard solid; processable |
| 11 | 10 | 90 | 110 | Hard solid; processable |
| 12 | 12.5 | 90 | 90 | Marginal/soft. Slow processing |
| Comparative F | 15 | 80 | 75 | Unacceptably soft, unprocessable |

As clearly seen from the Table, applicants have shown, contrary to what would previously been believed, that high levels of triglyceride (e.g., 6% and up) oil, can clearly be processed. However, as also seen from examples, at levels above 13%, the bars become unprocessable. Thus, applicants have found a clear criticality at levels of from 6 to 13% where bars are processable (e.g., have acceptable yield stress as defined) and maintain acceptable lather.

Example 13

In order to further demonstrate that the invention can be used with any triglyceride (i.e., is not limited to specific triglycerides), applicants compiled the following table showing various triglyceride oils together with lather and yield stress data within the scope of the invention:

| Oil | Lather, % | Yield Stress, Mpa |
|---|---|---|
| Apricot | 100 | 174 |
| Sunflower | 100 | 122 |
| Avocado Oil | 85 | 95 |
| Cottonseed | 85 | 136 |
| PKO | 80 | 95 |
| Safflower | 75 | 174 |
| Corn (refined) | 70 | 122 |
| Soya Bean | 70 | 136 |
| Almond Oil | 66 | 136 |
| Wheat Germ | 66 | 153 |

That is, all bars were acceptably processable when used at high levels (all oils were used at levels of 10%) in same 85/15 soap base as disclosed in Example A at Table 2.

Again, this clearly shows that any triglyceride soap or combination of triglyceride soaps having defined yield stress and lather volume can be used.

What is claimed is:

1. A process for making bar composition comprising:

(a) 59 to 84% by wt. soap;

(b) 0 to 10% by wt. non-soap, non-triglyceride agents;

(c) 10 to 18% by wt. water;

wherein said bar has yield stress of greater than about 90 and lather volume is at least 65% relative to base;

wherein said process comprises adding 6% to 13% triglyceride oil or oils to the bar at a finishing stage when other bar components have already crystallized.

2. A process according to claim 1, wherein triglyceride is selected from the group consisting of apricot oil, sunflower seed oil, avocado oil, cottonseed oil, palm kernel oil, safflower oil, corn oil, soybean oil, almond oil, wheat germ and mixtures thereof.

* * * * *